(12) United States Patent
Cohen et al.

(10) Patent No.: US 8,140,989 B2
(45) Date of Patent: Mar. 20, 2012

(54) VIRTUAL ROOM USE SIMULATOR AND ROOM PLANNING SYSTEM

(75) Inventors: Jason C. Cohen, Appleton, WI (US); Theodore T. Tower, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 331 days.

(21) Appl. No.: 12/388,955

(22) Filed: Feb. 19, 2009

(65) Prior Publication Data
US 2010/0211897 A1      Aug. 19, 2010

(51) Int. Cl.
*G06F 3/48* (2006.01)

(52) U.S. Cl. ........ 715/764; 715/757; 715/771; 715/700; 715/852; 703/1; 703/6; 703/22; 705/2

(58) Field of Classification Search .................... 715/764
See application file for complete search history.

(56) References Cited

U.S. PATENT DOCUMENTS

| | | | |
|---|---|---|---|
| 6,727,925 B1 | 4/2004 | Bourdelais | |
| 6,963,827 B1* | 11/2005 | Elyea et al. | 703/6 |
| 6,965,816 B2* | 11/2005 | Walker | 701/16 |
| 6,970,812 B2* | 11/2005 | Kamachi et al. | 703/6 |
| 7,062,722 B1 | 6/2006 | Carlin et al. | |
| 7,080,096 B1* | 7/2006 | Imamura | 1/1 |
| 7,099,752 B1* | 8/2006 | Lenell et al. | 701/2 |
| 7,139,685 B2* | 11/2006 | Bascle et al. | 703/1 |
| 7,277,572 B2 | 10/2007 | MacInnes et al. | |
| 7,301,547 B2 | 11/2007 | Martins et al. | |
| 2001/0002831 A1* | 6/2001 | Kato et al. | 345/326 |
| 2002/0065635 A1* | 5/2002 | Lei et al. | 703/1 |
| 2002/0091534 A1 | 7/2002 | Berning et al. | |
| 2002/0124295 A1* | 9/2002 | Fenwick et al. | 2/69 |
| 2005/0187677 A1* | 8/2005 | Walker | 701/16 |
| 2006/0111878 A1 | 5/2006 | Pendyala et al. | |
| 2006/0225205 A1* | 10/2006 | Troutman | 5/93.1 |

(Continued)

FOREIGN PATENT DOCUMENTS

JP          2002189764         7/2002

(Continued)

OTHER PUBLICATIONS

Virtual Nursery Planner, Babysdream <http://www.babysdream.com>, downloaded from wayback machine <http://web.archive.org> archived on Oct. 28, 2007.*

(Continued)

*Primary Examiner* — William Bashore
*Assistant Examiner* — Reza Nabi
(74) *Attorney, Agent, or Firm* — Dority & Manning, P.A.

(57) ABSTRACT

A room planning system for simulating the use of products during the performance of an activity in a room space is disclosed. The system includes a virtual room space comprising a virtual representation of an actual room space, an environment database having a collection of environment data defining attributes of the actual room space, and a product database having a collection of product data defining attributes of at least one product to be used for performing an activity in the room space. The system includes a user interface for selecting a virtual product and arranging the virtual product in the virtual room space. A simulation generator is programmed to simulate the performance of an activity in the virtual room space and to provide a feasibility analysis of the activity based at least in part on the arrangement of the virtual product in the virtual room space.

21 Claims, 11 Drawing Sheets

U.S. PATENT DOCUMENTS

| | | | |
|---|---|---|---|
| 2006/0229913 A1* | 10/2006 | Earle .................................. | 705/2 |
| 2008/0162261 A1 | 7/2008 | Velazquez et al. | |
| 2008/0162262 A1 | 7/2008 | Perkins | |
| 2009/0017430 A1* | 1/2009 | Muller-Daniels et al. .... | 434/262 |
| 2009/0100355 A1* | 4/2009 | Takemura et al. ............ | 715/757 |
| 2009/0112538 A1* | 4/2009 | Anderson et al. ................. | 703/6 |
| 2009/0112618 A1* | 4/2009 | Johnson et al. ................... | 705/2 |
| 2009/0113349 A1* | 4/2009 | Zohar et al. ................... | 715/852 |
| 2009/0119126 A1* | 5/2009 | Johnson et al. ................... | 705/2 |
| 2010/0157018 A1* | 6/2010 | Lampotang et al. ............ | 348/36 |
| 2011/0055746 A1* | 3/2011 | Mantovani et al. ........... | 715/771 |

FOREIGN PATENT DOCUMENTS

| | | |
|---|---|---|
| JP | 2004013500 | 1/2004 |

OTHER PUBLICATIONS

Reviews on Babyz, Published on Feb. 13, 2003 and Aug. 28, 2000, available online at <http://www.amazon.com/Babyz-Pc/dp/B00002DDN5/ref=sr_1_1?ie=UTF8&qid=1300801882&sr=8-1>, accessed on Mar. 19, 2011.*

Virtual Room Planner, Icovia <http://www.icovia.com>.*

* cited by examiner

VIRTUAL ROOM USE SIMULATOR AND ROOM PLANNING SYSTEM

BACKGROUND

Designing a room requires many different design choices, including the arrangement and orientation of furniture, appliances, and/or other fixtures in the room, the color of the walls, the type of flooring to be used within the room, the placement of artwork or other decorative elements in the room, the arrangement of lighting fixtures in the room, and importantly, the storage and configuration of products for performing activities in the room. These design choices are often based on various constraints such as room size, room layout, consumer preference, size of the furniture, appliances, and/or fixtures to be placed within the room, intended use of the room, price considerations and aesthetic considerations.

While everyone has a general idea of exactly how furniture should be placed within a room, there is also an assumption of where heavily used products should be placed based on aesthetic considerations. Unfortunately, by trial and error, it is usually discovered that those ideal locations, while aesthetically pleasing, are not the most efficient locations and can cause some serious problems. This can add stress as well as safety concerns depending on the situation.

For instance, parents expecting to bring a new born home may arrange a nursery room so that a diaper changing table, dresser, crib, chair, and diaper pail are arranged in a manner that is most aesthetically pleasing in the nursery room. Products used for changing a baby such as diapers, wipes, ointments, lotions, baby powder, paper towels, clothes, etc. may be stored in various locations throughout the nursery. For example, the diapers or baby's clothes may be stored out of sight in a drawer of a dresser located within the nursery.

After the parents bring the newborn home, the parents may realize that the original configuration of the nursery room is not feasible. For instance, while changing a baby, a parent or other consumer may realize that the diapers, wipes, or other products are located too far away from the changing table. This leads to inefficiency and safety concerns as the parent or supervisor will have to leave the baby alone on the changing table while retrieving the products from other areas of the nursery.

In addition, the drawer for storing diapers may only be able to store eight diapers at a time. Because most newborn babies use an average of ten diapers a day, the drawer is not the most ideal location for storing the diapers because it will require extra refill time to keep the diaper stocked. The contemplated arrangement of the nursery room simply is not feasible because it does not allow for the safe or efficient changing of a baby in the nursery room. The room will have to be physically rearranged in order to perform the baby changing activity safely and efficiently, leading to frustration.

The same sort of problems may arise with the arrangement of a bathroom space. Parents expecting to bring a newborn home may arrange products used for bathing a baby in various locations in a bathroom. For instance, the baby's shampoo, soap, and lotion may be located on a shelf next to the bath tub, the baby's toys may be arranged around the bath tub, and diapers for putting on the baby after the bath is finished may be arranged out of sight in a drawer in the bathroom. When the parent actually performs the activity of bathing the child, the parent may realize that the products used for bathing the baby are located beyond the reach of the parent. The parent will have to leave the baby alone in the bathtub to retrieve the product, raising serious safety concerns about leaving a newborn alone in a bath tub full of water. The products will have to be physically rearranged in the room to perform the activity of bathing the newborn safely. Parents may have to go through a period of trial and error until a safe and efficient arrangement of products is achieved.

Therefore, there is a need to develop an easy room planning system and method to simulate the environment, product placements, and use of a room prior to the real life conditions so that a consumer can analyze the feasibility of the room layout prior to physically arranging the room.

SUMMARY

One exemplary embodiment of the present disclosure is directed to a nursery room planning system. The system may include a virtual nursery room space comprising a virtual representation of an actual nursery room space, an environment database comprising a collection of environment data defining attributes of the actual nursery room space, and a product database comprising a collection of virtual products representative of products used for changing a baby. The nursery room planning system includes a user interface for selecting a virtual product and arranging the virtual product in the virtual nursery room space. A simulation generator is programmed to provide a simulation of the baby changing event and to provide a feasibility analysis of the baby changing event based at least in part on the arrangement of the virtual product in the virtual nursery room space.

In variations of this exemplary embodiment, the feasibility analysis may be based at least in part on safety constraints and/or efficiency constraints associated with the baby changing event. For instance, the feasibility analysis may comprise a determination of whether the virtual product is located outside a safety zone surrounding the location adjacent the baby changing event or a determination of the number of movements an individual will have to make during the baby changing event. The feasibility analysis may also include suggestions for alternative arrangements of the virtual product in the nursery room.

In other variations of this exemplary embodiment, the environment database may include a collection of virtual objects comprising virtual representations of furniture, appliances, or fixtures placed in the actual nursery room. The user interface may be configured to allow a user to select a virtual object and arrange the virtual object in the virtual nursery room space. The feasibility analysis may include suggestions for alternative arrangements for the virtual object in the nursery room space.

In still another variation of this exemplary embodiment, the environment database or the product database may be linked with a retailer information database. The environment database may also include user attribute data defining attributes of an anticipated user of the actual nursery room space. The simulation generator may be configured to provide a simulation and feasibility analysis based at least in part on the user attribute data. The simulation generator may also be configured to provide different feasibility analyses for different stages of development of a baby.

Another exemplary embodiment of the present disclosure is directed to a room planning system for simulating the use of products during the performance of an activity in a room space. The system includes a virtual room space comprising a virtual representation of an actual room space, an environment database having a collection of environment data defining attributes of the actual room space, and a product database having a collection of product data defining attributes of at least one product to be used for performing an activity in the room space. The system includes a user interface for selecting a virtual product and arranging the virtual product in the virtual room space. A simulation generator is programmed to simulate the performance of an activity in the virtual room space and to provide a feasibility analysis of the activity based at least in part on the arrangement of the virtual product in the virtual room space.

A further exemplary embodiment of the present disclosure is directed to a method for simulating use of a product during the performance of an activity in a room space. The method includes the steps of receiving a collection of environment data to include in a virtual room use simulation, the collection of environment data comprising attributes of a room space; receiving a collection of product data to include in a virtual room use simulation, the product data comprising attributes of products to be used for performing an activity in the room space; generating a virtual room space based on the collection of environment data, the virtual room space comprising a virtual representation of an actual room space; generating at least one virtual product based on the collection of product data, the at least one virtual product comprising a virtual representation of an actual product to be used for performing the activity; arranging the virtual products in the virtual room space; generating a simulation of the activity; generating a feasibility analysis of the activity based at least in part on the arrangement of the virtual product in the virtual room space; and displaying the simulation and the feasibility analysis to a user.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
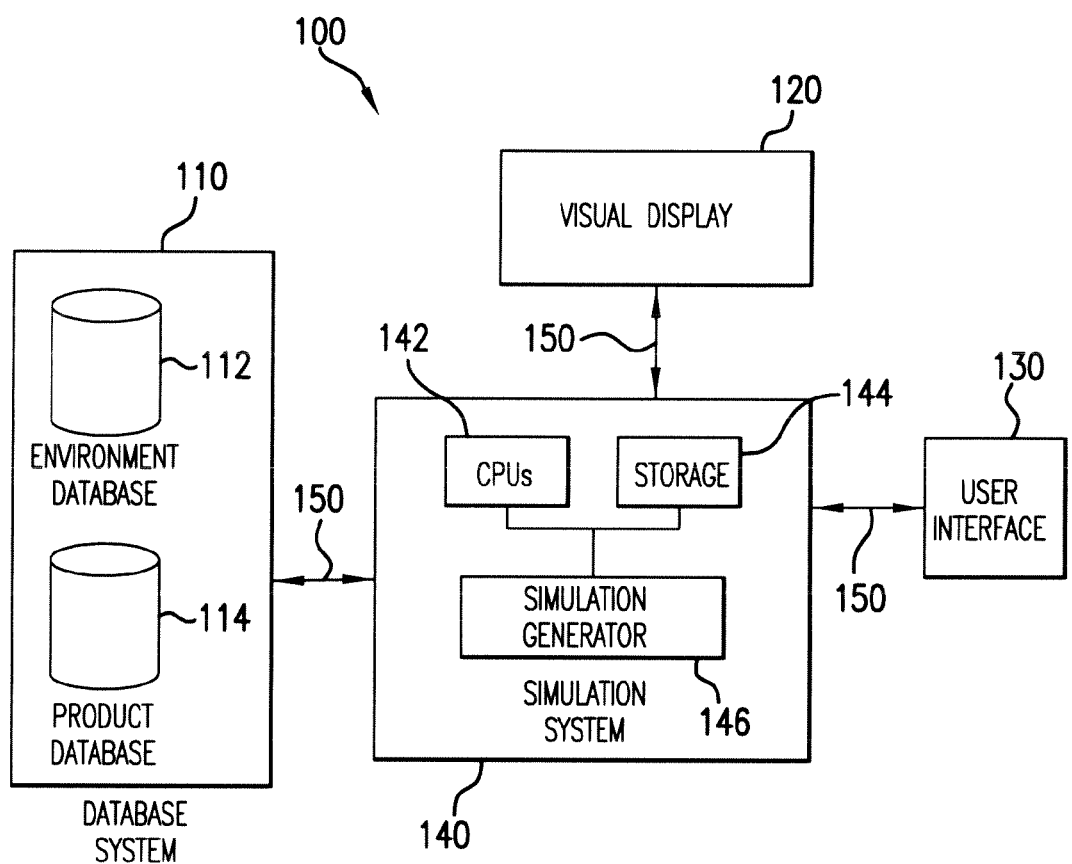
FIG. 1 provides a conceptual illustration of a room planning system according to an exemplary embodiment of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

The technology discussed herein makes reference to servers, databases, software applications, and other computer-based systems, as well as actions taken and information sent to and from such systems. One of ordinary skill in the art will recognize that the inherent flexibility of computer-based systems allows for a great variety of possible configurations, combinations, and divisions of tasks and functionality between and among components. For instance, server processes discussed herein may be implemented using a single server or multiple servers working in combination. Databases and applications may be implemented on a single system or distributed across multiple systems. Distributed components may operate sequentially or in parallel.

When data is obtained or accessed between a first and second computer system or component thereof, the actual data may travel between the systems directly or indirectly. For example, if a first computer accesses a file or data from a second computer, the access may involve one or more intermediary computers, proxies, and the like. The actual file or data may move between the computers, or one computer may provide a pointer or metafile that the other computer uses to access the actual data from a still further computer.

The various computer systems discussed herein are not limited to any particular hardware architecture or configuration. Embodiments of the methods and systems set forth herein may be implemented by one or more general-purpose or customized computing devices adapted in any suitable manner to provide desired functionality. The device(s) may be adapted to provide additional functionality complementary or unrelated to the present subject matter, as well. For instance, one or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including, but not limited to application-specific circuits. Of course, combinations of computer-executed software and hard-wired logic or other circuitry may be suitable, as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the computer(s) to implement one or more embodiments of the methods of the present subject matter. Additionally or alternatively, the computing device(s) may comprise circuitry that renders the device(s) operative to implement one or more of the methods of the present subject matter. Furthermore, components of the presently-disclosed technology may be implemented using one or more computer-readable media.

Any suitable computer-readable medium or media may be used to implement or practice the presently-disclosed subject matter, including, but not limited to, diskettes, drives, and other magnetic-based storage media, optical storage media, including disks (including CD-ROMS, DVD-ROMS, and variants thereof), flash, RAM, ROM, and other memory devices, and the like.

The present disclosure also makes reference to the relay of communicated data over one or more communications networks. It should be appreciated that network communications can comprise sending and/or receiving information over one or more networks of various forms. For example, a network can comprise a dial-in network, a local area network (LAN), wide area network (WAN), public switched telephone network (PSTN), the Internet, intranet or other type(s) of networks. A network may comprise any number and/or combination of hard-wired, wireless, or other communication links.

The present disclosure refers to room planning systems and room use simulators. A room planning system or room use simulator is any device or method that simulates activity in a room space. For instance, the room planning system or room use simulator may be used to simulate the changing of a baby in a nursery. In other embodiments, the room planning system or room use simulator may be used to simulate the performance of a medical operation in an operating room. Still other embodiments may include simulating bathing a baby in a bathroom space, preparing a meal in a kitchen space, machining of material in a manufacturing space, and/or storage of material in a storage space. Using the teachings disclosed herein, those of ordinary skill in the art should understand that of the present disclosure is not limited to the simulation of any particular activity in any particular room space, but is rather intended to encompass the simulation of all types of activities in all varieties of room spaces.

Embodiments of the present disclosure include methods, apparatus, and systems for generating a simulation of an activity performed in a room space in order to analyze the feasibility of performing the activity based at least in part on the configuration of the room space and the arrangement of products used for performing activity in the room space. The simulation and feasibility analysis provided by the system and methods of the present disclosure allow for an individual to determine the most efficient and/or safe layout for a particular room space prior to actually physically arranging the room space and performing the activity.

The present disclosure is directed to a room planning system for simulating the use of products during the performance of an activity in a room space. The system includes a virtual room space comprising a virtual representation of an actual room space, an environment database having a collection of environment data defining attributes of the actual room space, and a product database having a collection of product data defining attributes of at least one product to be used for performing an activity in the room space. The system includes a user interface for selecting a virtual product and arranging the virtual product in the virtual room space. A simulation generator is programmed to simulate the performance of an activity in the virtual room space and to provide a feasibility analysis of the activity based at least in part on the arrangement of the virtual product in the virtual room space. In this manner, the virtual room use simulator allows an individual to test the feasibility of a particular room layout prior to actually physically arranging the room space and performing the activity in the room space.

For instance, the virtual room use simulator may be a nursery room planning system for simulating the changing of a baby in the nursery room. The system can include a virtual nursery room space comprising a virtual representation of an actual nursery room space, an environment database comprising a collection of environment data defining attributes of the actual nursery room space, and a product database comprising a collection of virtual products used for changing a baby. The virtual products may comprise virtual representations of, for instance, diapers, baby wipes, disposable tissue, baby powder, lotions, ointments, baby's clothes, or other items used for changing a baby. The nursery room planning system includes a user interface for selecting a virtual product and arranging the virtual product in the virtual nursery room space. A simulation generator is programmed to provide a simulation of the baby changing activity and to provide a feasibility analysis of the baby changing activity based at least in part on the arrangement of the virtual product in the virtual room space.

The feasibility analysis can be based on variety of safety constraints and/or efficiency constraints. For instance, the feasibility analysis can determine whether a product used for changing a baby is located within a safety zone surrounding the location adjacent to where the baby changing occurs. The feasibility analysis can also determine the number of movements an individual will have to make during the baby changing activity based on the arrangement of the virtual products in the virtual nursery room. In this manner, a user may test the feasibility of a particular nursery room layout and the arrangement of products for changing a baby in the room prior to actually physically arranging the nursery and changing a baby in the nursery room. This tool can be particularly useful for new parents who have never experienced changing a baby and may not be aware of any particular safety or efficiency concerns prior to actually changing a baby in the room.

The input data used to create the simulation and feasibility analysis may be obtained from a variety of sources. For instance, users may provide information about the room space, for example, by submitting photographs, CAD drawings, etc. In other embodiments, users may configure the layout of the virtual room space by manually inputting various parameters of the room space, including square footage, wall dimensions, etc. In still other embodiments, a user may draw a virtual representation of a room space using an input tool, such as a mouse, drawing pad, touch screen or keyboard.

In alternative embodiments, the input data may be retrieved from a retail database. For instance, retailers such as Babies R Us®, Target®, etc. may provide a database defining attributes of various pieces of furniture, appliances, fixtures, or products sold by the retail outlet. The room planning system may be linked to the retail database so that a user may retrieve various data defining attributes of a room layout or product to be used in the room from the retail database. For instance, a user may anticipate placing a changing table sold by Target® in a nursery room. The user may retrieve data defining attributes of the changing table from the Target® retail database. The room planning system may then generate a simulation and feasibility analysis based at least in part on the various attributes of the particular changing table sold by Target®.

For example, the changing table sold by Target® may include two drawers, each with the capability of storing eight newborn diapers. The feasibility analysis may determine that the storage of diapers in only one of the drawers may not be the most efficient room configuration because a newborn baby uses an average of ten diapers a day. The room planning system may provide a suggestion for using both drawers of the changing table to store newborn diapers in order to reduce restocking time.

Additional input data used to create the simulation and feasibility analysis may be based on user attribute data. User attribute data define attributes of the person and/or persons to be performing the activity in the room space. For instance, user attribute data may include the height, weight, sex, age, and other information about a person. The user attribute data may be input by a variety of means by either manually inputting the information or automatically determining the information through various scanning devices. The systems and methods of the present disclosure can utilize the user attribute data to tailor a simulation and feasibility analysis to a specific anticipated user.

Referring now to FIG. 1, a conceptual illustration of one embodiment of a room planning system 100 according to the present disclosure is illustrated. Using the teachings disclosed herein, one of ordinary skill in the art should understand that the arrangement of the room planning system 100 disclosed in FIG. 1 can be modified to suit individual circumstances. The system 100 generally includes a database system 110, visual display 120, user interface 130, and simulation system 140. The individual components of the system 100 are operatively connected by communications medium 150. The various components of the system 100 may be representative of various system components, e.g. desktop computers, server computers, laptop computers, tablet computers, and the like. Embodiments of the present disclosure are not limited to any particular computing system, application, device, or network architecture, and may be adapted to take advantage of new computing systems and platforms as they become available.

Communications medium 150 is intended to be representative of any medium for transferring data between the various components of the system 100. Communications medium 150 may take any form, whether integrated, distributed, wired, wireless, etc. For instance, communications medium 150 may be the Internet, an intranet, a local area network (LAN), wide area network or the like.

Simulation system 140 includes CPUs 142, storage 144, and simulation generator 146. CPU 142 is a programmable logic device that executes the instructions, logic and mathematical processing performed in executing user applications (e.g. simulation generator 146). Storage 144 stores application programs and data for use by simulation system 140. Common storage devices include hard-disk drives, flash memory devices, optical media and the like.

Simulation system 140 is configured to generate a simulation and feasibility analysis of an activity to be performed in a room space and to display the simulation and feasibility analysis to a user of the room planning system 100 through visual display 120. Visual display 120 can be any device adapted to display the simulation and feasibility analysis of the activity to a user. For example, the visual display 120 may be a monitor or screen operatively connected to the room planning system 100. Alternatively, the visual display 120 may be incorporated into a web-browser configured to display multimedia content. For instance, a user may access the room planning system 100 remotely via an Internet web-browser. The user may interact with the room planning system and view the simulation and feasibility analysis of the activity through visual display 120 incorporated into the web-browser.

Individuals may interact with the system 100 using a variety of different user interfaces 130. For instance, the user interface 130 can be a personal computer, desktop computer, notebook computer, personal digital assistant (PDA), WebTV (or other Internet only terminal), cell phone, screen phone, in-store kiosk, or other known communication device. The user interface 130 is configured to execute one or more computer programs, such as an Internet browser program, to allow users to interact with the system 100. In one embodiment, the user interface 130 is in the form of a personal computer located at a user's home. In another embodiment, the user interface 130 may be in the form of a kiosk located in a retail store. In this embodiment, a consumer may receive a simulation and feasibility analysis of an anticipated room layout while shopping at the retail store. The simulation and feasibility analysis may aid the consumer in making purchase decisions for furniture, appliances, or fixtures to be placed in a room space.

Database system 110 is used to store a collection of environment data 112 and product data 114. Environment data 112 and product data 114 are used by simulation system 140 to generate a simulation of an activity to be performed in the room space. The database system 110 may be located remotely from simulation system 140 and operatively connected to the simulation system 140 through communications medium 150. In the alternative, the database system may be arranged as part of or integral with the simulation system 140.

Environment data 112 is used by the simulation generator to generate a virtual room space that is representative of an actual room space. Environment data 112 may define, among other things, various attributes of the virtual room space generated by simulation system 140. For instance, environment data 112 may include descriptions of room layout such as locations of walls, closets, doorways, floor space, etc.

In addition, environment data 112 may include virtual objects to be arranged in the virtual room space. These virtual objects include virtual representations of furniture, appliances, and or fixtures to be included in the virtual room space. For instance, if the virtual room space comprises a virtual representation of a nursery room, the virtual objects may include a crib, changing table, dresser, end table, chair, or other item of furniture to be placed in the nursery room space. If the virtual room space comprises a virtual representation of a kitchen, the virtual objects may include cabinets, refrigerator, range, oven, dishwasher, counters, tables, or other furniture items, appliances, or fixtures to be located in the simulated kitchen space.

In particular embodiments, the user interface 130 is configured to allow a user to select virtual objects and arrange them in the virtual room space. For instance, in the simulation of a nursery room, a user may select a virtual crib, chair, and changing table and arrange the virtual crib, chair, and changing table in the virtual nursery room space in accordance with an anticipated room layout. The simulation system 140 then generates a simulation of a baby changing event and provides a feasibility analysis based at least in part on the particular arrangement of the crib, chair, and changing table in the nursery room. If the user of the system 100 determines that the particular arrangement is no longer desirable based on the simulation and the feasibility analysis, the user may reconfigure the virtual objects in the virtual room and direct the simulation generator to provide a new simulation and feasibility analysis based on the new room layout. By allowing a user to virtually rearrange an anticipated room layout to meet efficiency and safety constraints, the hassle associated with repeatedly physically rearranging a room can be avoided.

Environment data may also include user attribute data defining specific attributes of the person and/or persons to be performing the activity in the room space. For instance, user attribute data may include the height, weight, sex, age, and/or other information about a person. This data may be used generate a simulation and feasibility analysis based on various physical attributes of an anticipate user.

For example, a six foot tall male has a much larger arm span than a five foot six inch tall female. A room planning system providing a simulation and feasibility analysis of a baby changing event in a nursery room space may consider the larger arm span in analyzing the feasibility of the baby changing event. Moreover, the room planning system may indicate that an anticipated room layout is feasible for one particular user, but not necessarily feasible for another user based on characteristics of the particular users. In this manner, the room planning system 100 of the present disclosure can tailor the simulation and feasibility analysis to specific individuals.

Environment data 112 may be received or collected from a variety of sources. In one embodiment, the user of the room planning system 100 inputs the environment data through user interface 130. For instance, the environment data may be retrieved from photographs, CAD drawings, etc. supplied by the user. In other embodiments, a user may configure the layout of the virtual room space by manually inputting various parameters of the room space through user interface 130, including square footage, wall dimensions, etc. In still other embodiments, a user may draw a virtual representation of a room space using an input tool, such as a mouse, drawing pad, touch screen or keyboard.

Virtual object data, i.e. data representative of furniture, appliances, or fixtures to be arranged in the virtual room space, may also be derived from a plurality of sources. In one embodiment, the user simply selects a virtual object from a library of virtual objects stored in the environment database 112. The user may then arrange the virtual object as desired in the virtual room space. In other embodiments, the user may draw various virtual objects in the virtual room space via user interface 130.

In still other embodiments, virtual object data is received from a retail database. The retail database will define various attributes of a particular item of furniture, appliance, or other fixture sold by a retail outlet. If a consumer anticipates purchasing the particular item of furniture, appliance, or other fixture, the consumer may receive a virtual representation of the particular item of furniture, appliance, or fixture and arrange the virtual object in the virtual room space. The simulation and feasibility analysis of the activity to be performed in the room space will be based at least in part on the various attributes received from the retail database.

Database system 110 also includes product data 114. Product data defines attributes of virtual products comprising virtual representations of products to be used while performing an activity in a virtual room space. For instance, if the system 100 simulates the changing of a baby in a nursery room, the virtual products may comprise virtual representations of diapers, wipes, ointments, lotions, baby powder, paper towels, clothes, etc., used for changing a baby. If the system 100 is used to simulate a surgical procedure in an operating room, the virtual products may include virtual representations of surgical instruments, scalpels, forceps, clamps, distractors, lancets, syringes, suction tubes, calipers, optical devices, bandages, gauzes, or other medical devices or instruments to be used during the simulated surgical procedure. Product data may include the product itself, product features, product packaging, and the like.

User interface 130 allows a user to select virtual products and arrange them in the virtual room space. For instance, in the simulation of a nursery room, a user may arrange virtual products representative of diapers in a drawer of a virtual dresser located in the virtual room space. The simulation system 140 will generate a simulation of a baby changing activity and provide a feasibility analysis of the baby changing activity based in part on the arrangement of the diapers in the drawer. In another embodiment, for example, the virtual room space may comprise a virtual representation of an operating room. The user may select and arrange virtual products representative of surgical instruments and other items to be used during an operating procedure. The system 100 will generate a simulation and feasibility analysis of the operating procedure based on the arrangement of the virtual products in the operating room space.

Product data 114 can be received from a variety of sources. In one embodiment, the user simply selects a virtual product from a library of virtual objects stored in the product database 114. The user may then arrange the virtual object as desired in the virtual room space. In other embodiments, the user may draw various virtual products in the virtual room space via user interface 130. In still other embodiments, virtual product data is received from a retail database. Once received, the user of the system 100 may arrange the virtual products throughout the virtual room space using user interface 130.

Simulation generator 146 is configured to generate a simulation of an activity to be performed in the room space. The simulation of the activity may be interactive, allowing a user to control the simulation as it is taking place. For instance, in the simulation of a baby changing event in a virtual nursery room space, the user may be able to direct a virtual representation of a person to perform the following tasks: (1) pick up a virtual representation of a baby; (2) carry the virtual baby to a virtual changing table; (3) change the virtual baby using various virtual products located in the room space; and (4) place the virtual baby in a crib after the virtual baby has been changed. By having an interactive simulation, a user of the room planning system may experience first hand how efficient of a design they have developed.

The simulation generator 146 is also programmed to provide a feasibility analysis of the simulated activity. The feasibility analysis can be based on safety constraints and/or efficiency constraints. Safety constraints define parameters by which the simulated activity can be performed safely based on variables including room layout, type of activity being simulated, arrangement of virtual objects in the virtual room space, user attribute data, and arrangement of virtual products in the virtual room space. For instance, for safety considerations, a baby cannot be left alone on a changing table while a parent travels to another part of the room to obtain a product used for changing a baby. To address this safety issue, the room planning system may provide a feasibility analysis indicating whether a virtual product used for changing a baby is located within a safety zone surrounding the area where the simulated baby changing event takes place. If a virtual product is located outside of the safety zone, the room planning system 100 will provide an indication to the user that the current room layout and arrangement of products in the room is not feasible for safety reasons. The user of the room planning system may then rearrange the virtual objects and virtual products in the room space until a feasible room layout is achieved. In the alternative, the simulation generator 146 may suggest an alternative room layout and configuration of products.

The feasibility analysis may also be based on a variety of efficiency constraints. Efficiency constraints define parameters by which the simulated activity can be performed efficiently based on variables including room layout, type of activity being simulated, user attribute data, arrangement of virtual objects in the virtual room space, and arrangement of virtual products in the virtual room space. For instance, the feasibility analysis may determine the number of movements required to change a baby based on the arrangement of products in the virtual room space. If the number of movements exceeds a certain threshold number, the room planning system 100 may provide an indication that the current room layout and arrangement of products in the room is not feasible for efficiency reasons. The user of the room planning system may then rearrange the virtual objects and virtual products in the room space until a feasible room layout is achieved. In the alternative, the room planning system 100 may suggest an alternative room layout and configuration of products.

The feasibility analysis may also be progressive based on, for instance, different stages of development of a newborn or child. For instance, in a nursery room, a particular storage location for diapers may be an efficient storage location for the smaller diapers required for a newborn baby. However, the same storage location may not be efficient eight months later for storing the larger diapers required for an eight-month old baby. To address these differences, the room planning system 100 may provide a plurality of different simulations and feasibility analyses based on different stages of development for a baby. For example, the room planning system may provide an indication that a particular room arrangement is feasible for a newborn child, but not for an eight-month old child.

The feasibility analysis is not limited to any particular type of safety and/or efficiency constraints. The present disclosure is intended to encompass any analysis of the simulated activity to determine whether the activity can be performed safely and efficiently based on the room layout, configuration of products within the room, user attributes, and/or different stages of development. For instance, the feasibility analysis can determine whether a particular item of furniture is suitable for storing a product used for performing the activity in the room space. The feasibility analysis can also determine whether the arrangement of products present additional hazards, such as being placed in a location where a person might trip over the product.

Figure 2:
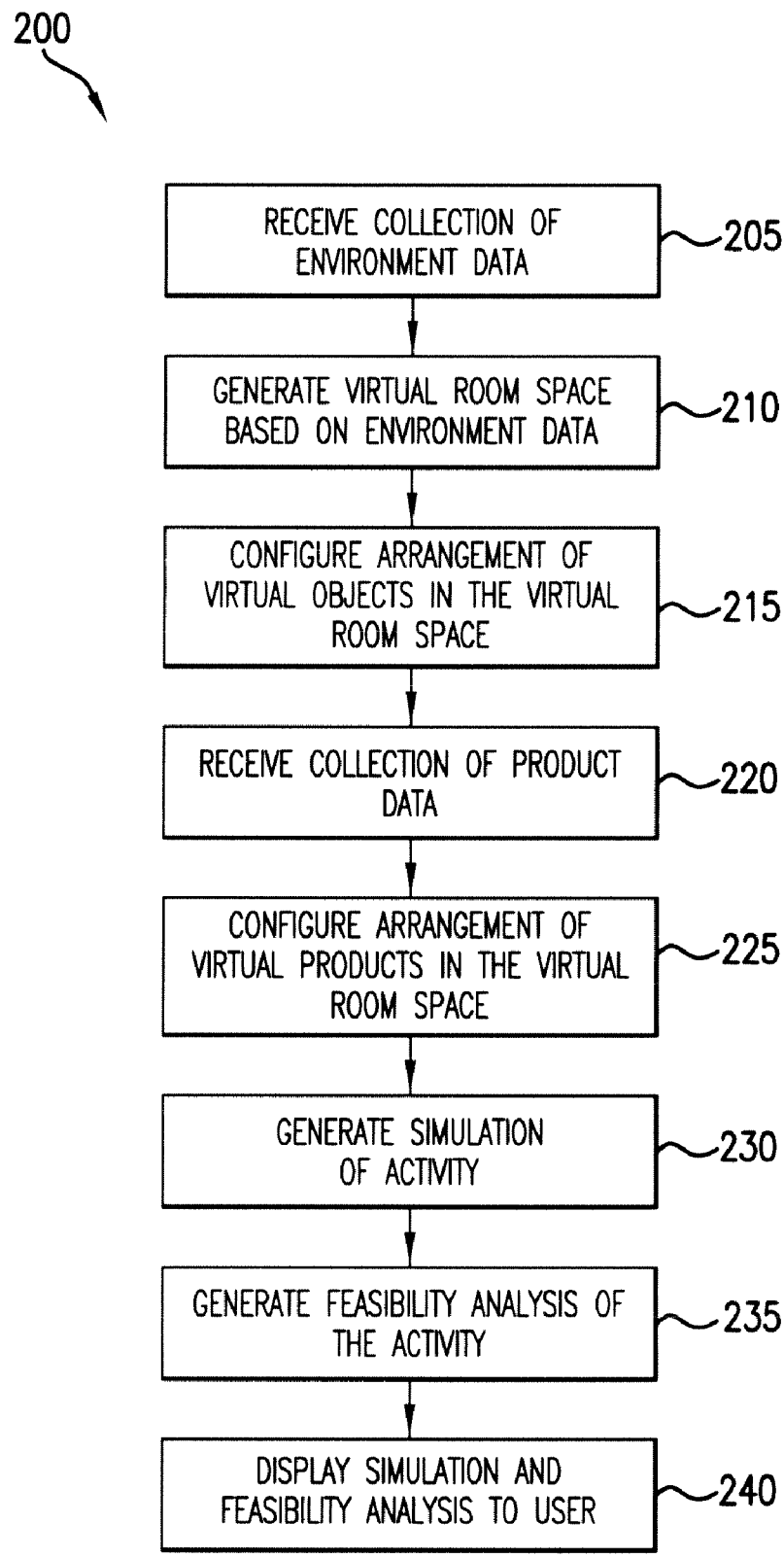
FIG. 2 provides a flow diagram of the exemplary steps associated with a method according to the present disclosure.

FIG. 2 provides a flow chart illustrating the exemplary steps associated with a method for simulating use of a product during the performance of an activity in a room space. As shown, the method 200 begins at step 205, where environment data defining attributes of a virtual room space and objects to be placed within the room space are specified. For instance, the environment data may be retrieved from photographs, CAD drawings, etc. supplied by a user. In other embodiments, a user may configure the layout of the virtual room space by manually inputting various parameters of the room space through a user interface, including square footage, wall dimensions, etc. In still other embodiments, a user may draw a virtual representation of a room space using an input tool, such as a mouse, drawing pad, touch screen or keyboard. Virtual object data, i.e. data representative of furniture, appliances, or fixtures to be arranged in the virtual room space, may also be derived from a plurality of sources. In one embodiment, the user simply selects a virtual object from a library of virtual objects stored in the environment database. In other embodiments, the user may draw various virtual objects in the virtual room space via user interface. In still other embodiments, virtual object data is received from a retail database.

At step 210, a virtual room space comprising a virtual representation of an actual room space is generated based on the collection of environment data. The virtual room space may comprise a virtual representation of a variety of different types of room spaces, including, for instance, nursery room space, storage room space, bathroom space, kitchen/food preparation room space, operating room space, machine shop space, manufacturing facility space, etc. At step 215, a variety of virtual objects comprising virtual representations of furniture, appliances, and/or fixtures are arranged in the virtual room space. For example, a user may arrange virtual objects representative of a crib, dresser, and changing table in a nursery room space. In another embodiment, a user may arrange virtual objects representative of equipment in a manufacturing room space.

At step 220, product data defining attributes of virtual products representative of products used for performing an activity in the room space are specified. For instance, if the simulated activity is changing a baby in a nursery room space, product data defining attributes of virtual products representative of diapers, wipes, ointments, lotions, baby powder, paper towels, clothes, etc., used for changing a baby are specified. If the simulated activity is bathing a baby in a bathroom, product data defining attributes of virtual products representative of soap, shampoo, bathroom toys, towels, clothes, etc. used while bathing a baby are specified. At step 225, the virtual products are arranged in the virtual room space. For instance, a user may arrange virtual products representative of diapers in a dresser drawer. In another embodiment, a user may arrange virtual products representative of a baby's clothes on the top shelf of a closet.

At step 230, the method generates a simulation of an activity to be performed in the room space. The activity may include, for instance, the changing of a baby in a nursery room space, the bathing of a baby in a bathroom space, the performance of a surgical operation in an operating room, the machining of an apparatus in a manufacturing space, the preparation of food in a kitchen, etc. At step 235, the method provides a feasibility analysis of the simulated activity. The feasibility analysis may be based on various safety constraints and/or efficiency constraints. For example, the feasibility analysis may determine whether the a baby can be bathed in a bathroom space without having to leave the baby alone in the bathtub while products used for bathing the baby are retreived.

At step 240, the simulation and the feasibility analysis are displayed to a user. Based on the simulation and the feasibility analysis, the user may virtually rearrange the virtual objects and virtual products in the room space until a safe and efficient layout is obtained. Alternatively, an ideal room layout may be suggested to the user. In this manner, the method of the present disclosure allows a user to determine a safe and efficient arrangement of a room space without having to go through the hassle of physically rearranging objects and products in the room.

EXAMPLE

Figure 3A:
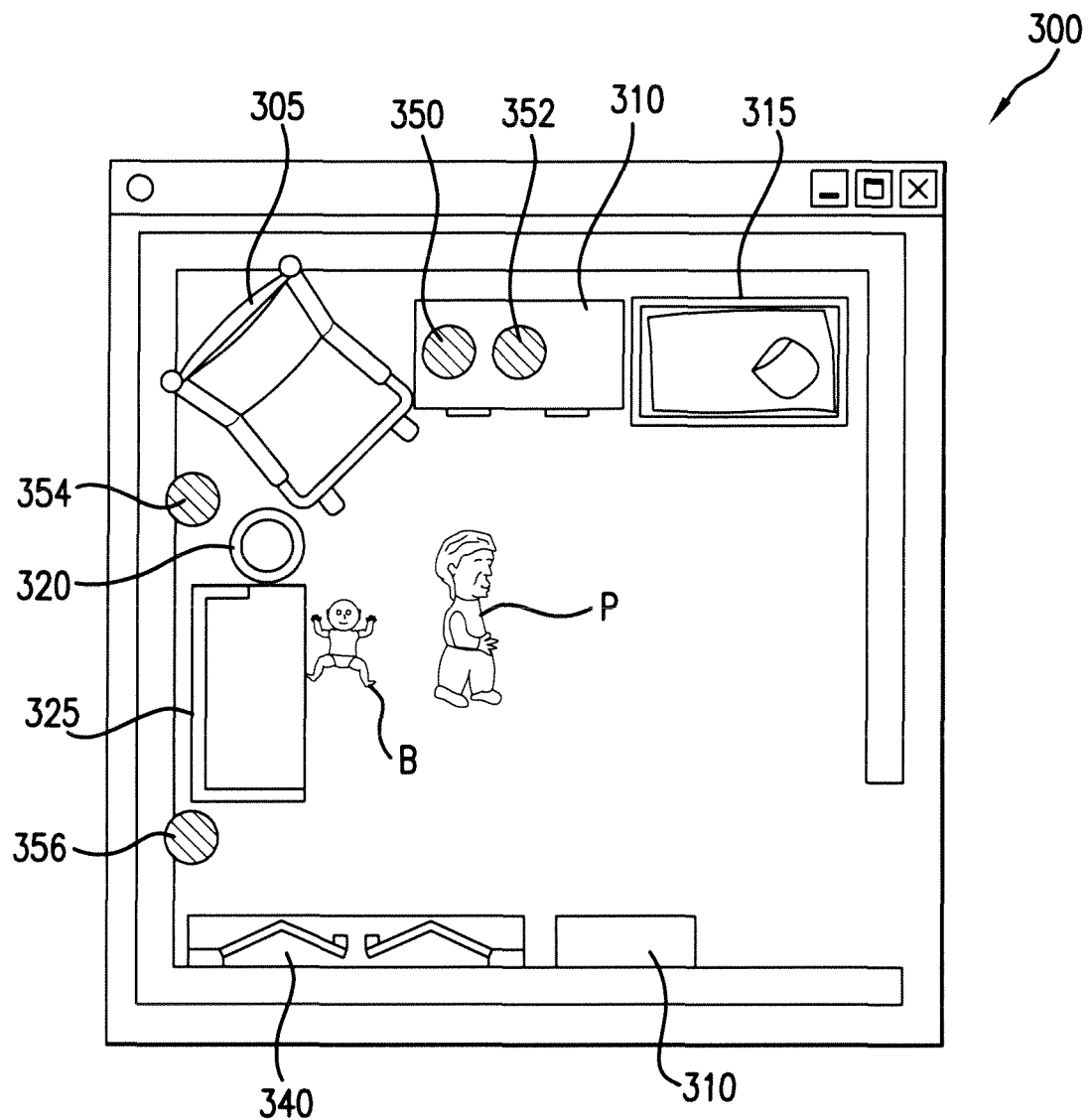
FIGS. 3a-3i provide screen shots of an exemplary visual display according to an exemplary embodiment of the present disclosure.

With reference now to FIGS. 3a-3i, an exemplary embodiment of the present disclosure will be explained by way of example. The exemplary embodiment illustrated in FIG. 3a depicts an exemplary visual display of a room planning system used to simulate a baby changing event in a nursery room. The simulation depicted in FIGS. 3a-3i is interactive, allowing a user, for instance, to direct parent P to change baby B after the baby B starts crying.

FIG. 3a depicts a virtual nursery room space 300 comprising a virtual representation of an actual nursery room. A variety of virtual objects have been arranged in virtual room 300. For instance, virtual objects representing a chair 305, dressers 310, crib 315, diaper pail 320, and changing table 325 are arranged in the virtual nursery room space 300. The virtual room space includes closet space 340. A variety of virtual products 350, 352, 354, and 356 have been arranged in various locations throughout the virtual room space. Virtual products 350, 352, 354, and 356 are virtual representations of products used by parent P to change baby B and may be representative of diapers, wipes, ointments, lotions, baby powder, paper towels, clothes, etc., used for changing a baby. The virtual products 350, 352, 354, and 356 in this exemplary embodiment are depicted as balls with diagonal cross-hatching. However, any virtual representation of the products falls within the scope and spirit of the present disclosure.

Figure 3B:
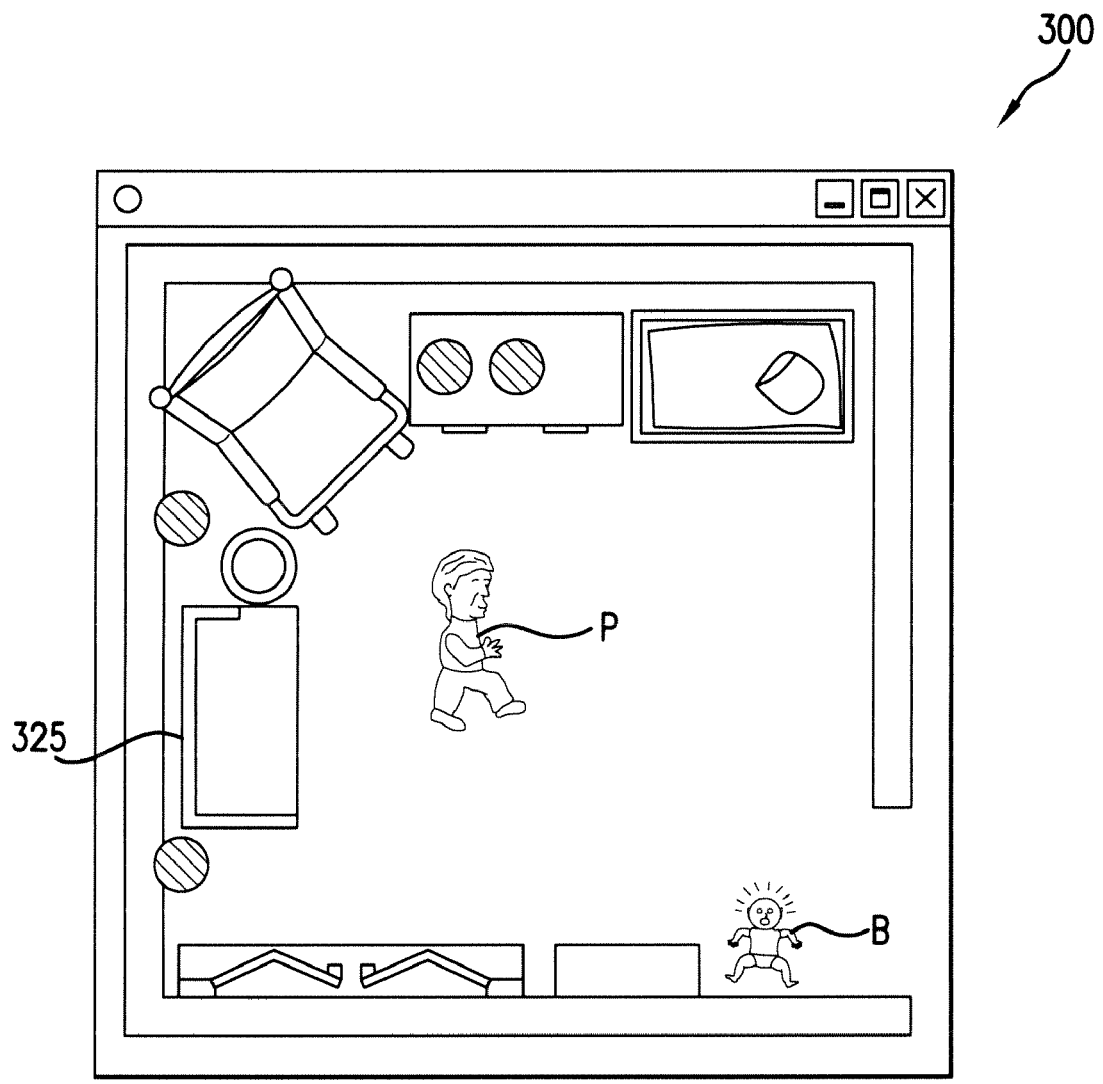
Figure 3C:
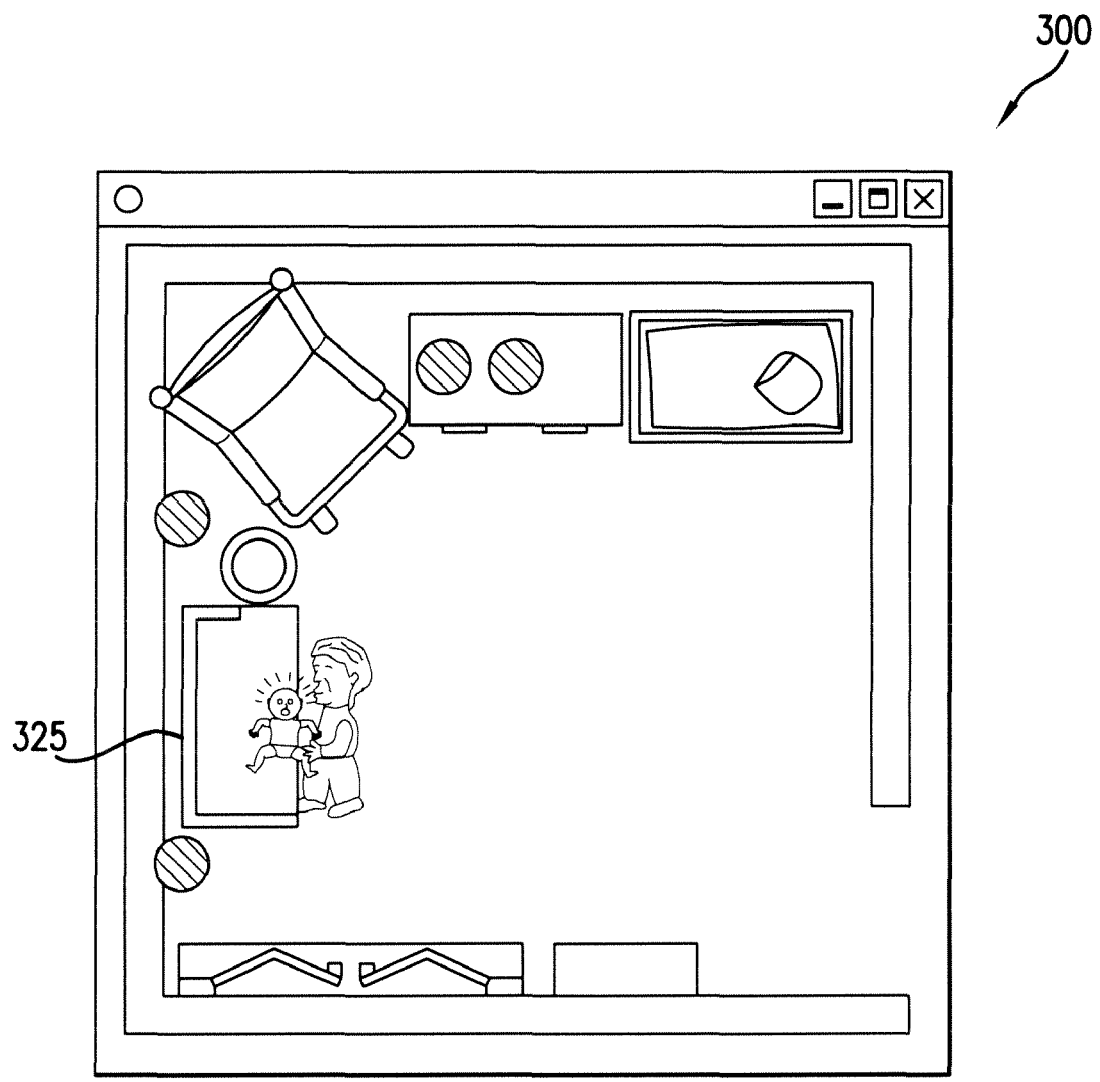

FIG. 3b depicts a screen shot after the system has caused the baby B to start crying. To stop the baby from crying, the user must direct parent P to pick up the baby, carry the baby to the changing table, and perform the baby changing activity on the changing table. FIG. 3c depicts a screen shot after the user has directed parent P to pick up the crying baby B and place him on the changing table 325.

Figure 3D:
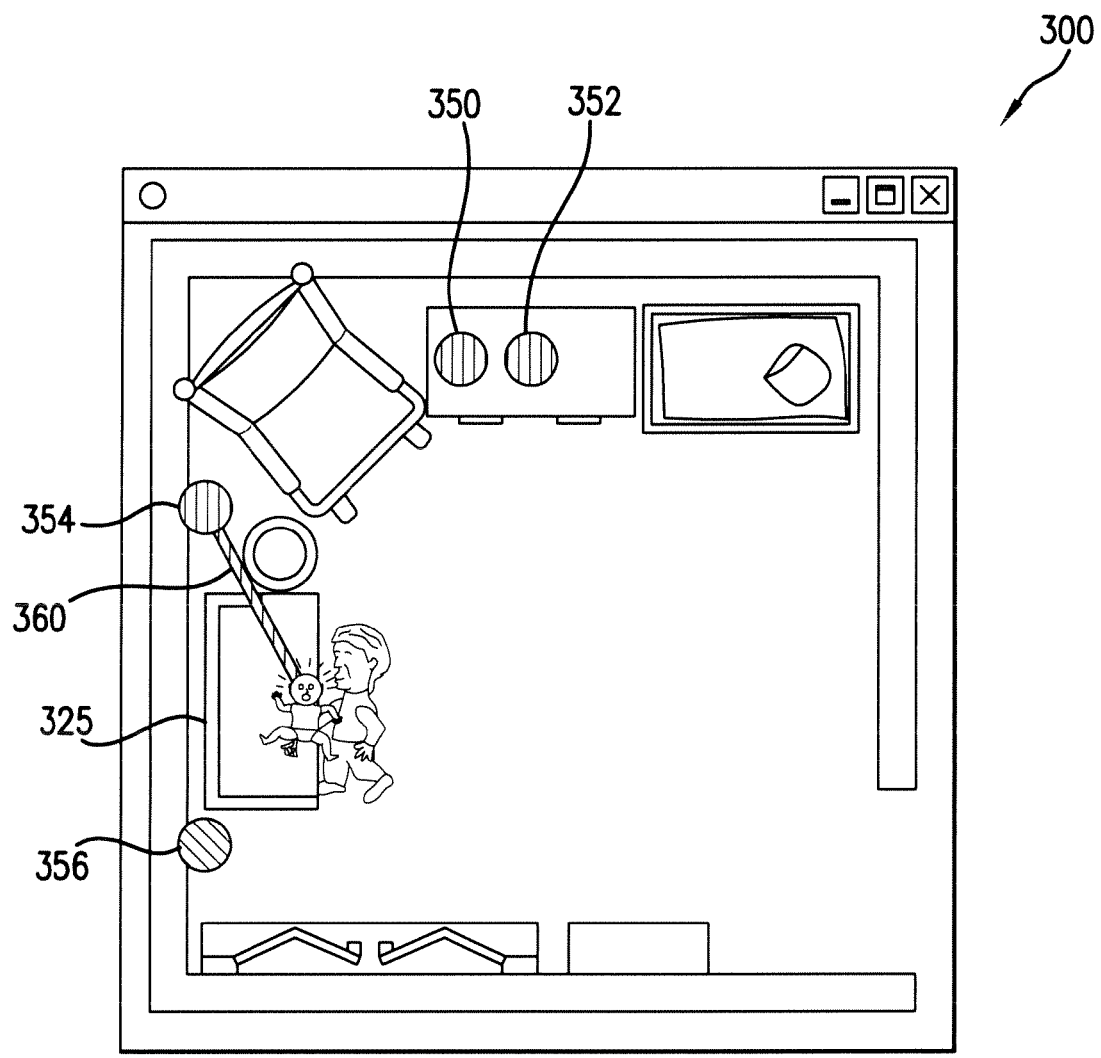
Figure 3E:
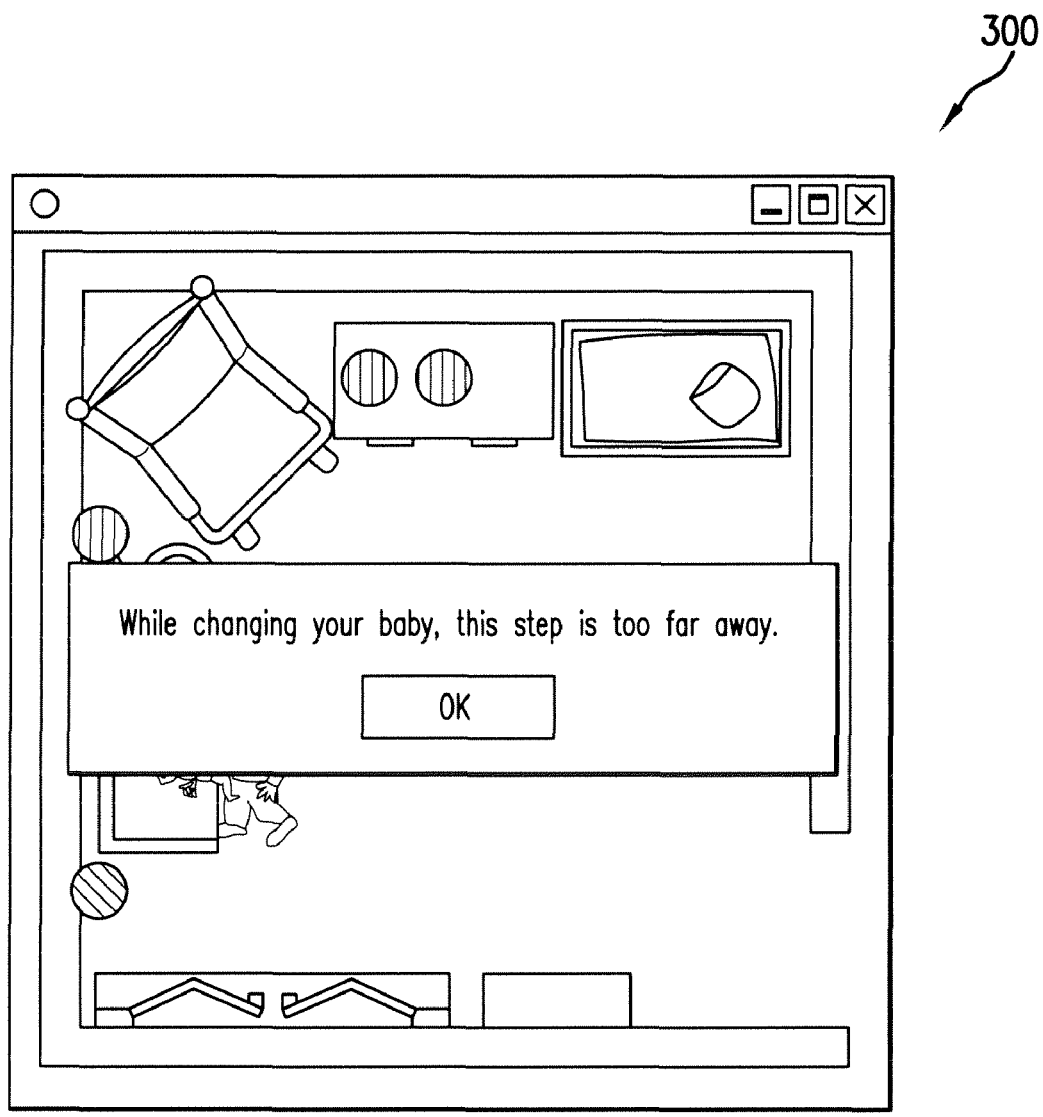

After the baby B is placed on the changing table, the simulation generator provides a simulation and a feasibility analysis of the baby changing activity. FIG. 3d depicts a screen shot presenting the results of the feasibility analysis to the user. The cross-hatched line 360 indicates that the virtual product 354 is located too far away for the baby changing event to be performed safely and efficiently. The virtual products 350 and 352 are also depicted as balls having vertical cross-hatching to indicate that they are located too far away from the changing table 325. Virtual product 356 with diagonal cross-hatching is located at a safe and efficient location. As shown in FIG. 3e, the room planning system informs the user that some of the virtual products used for changing the baby are located too far away from the changing table.

Figure 3F:
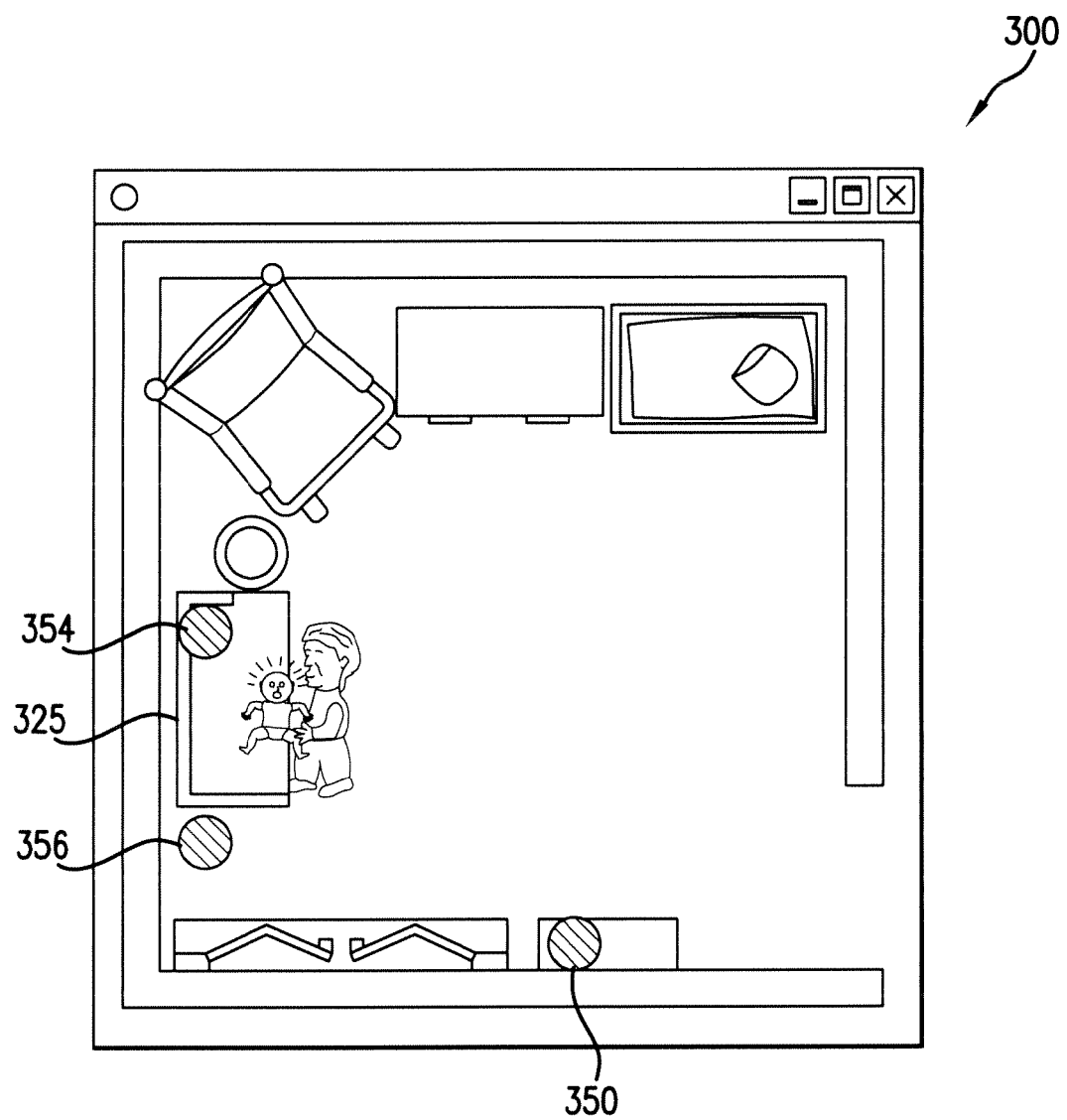
Figure 3G:
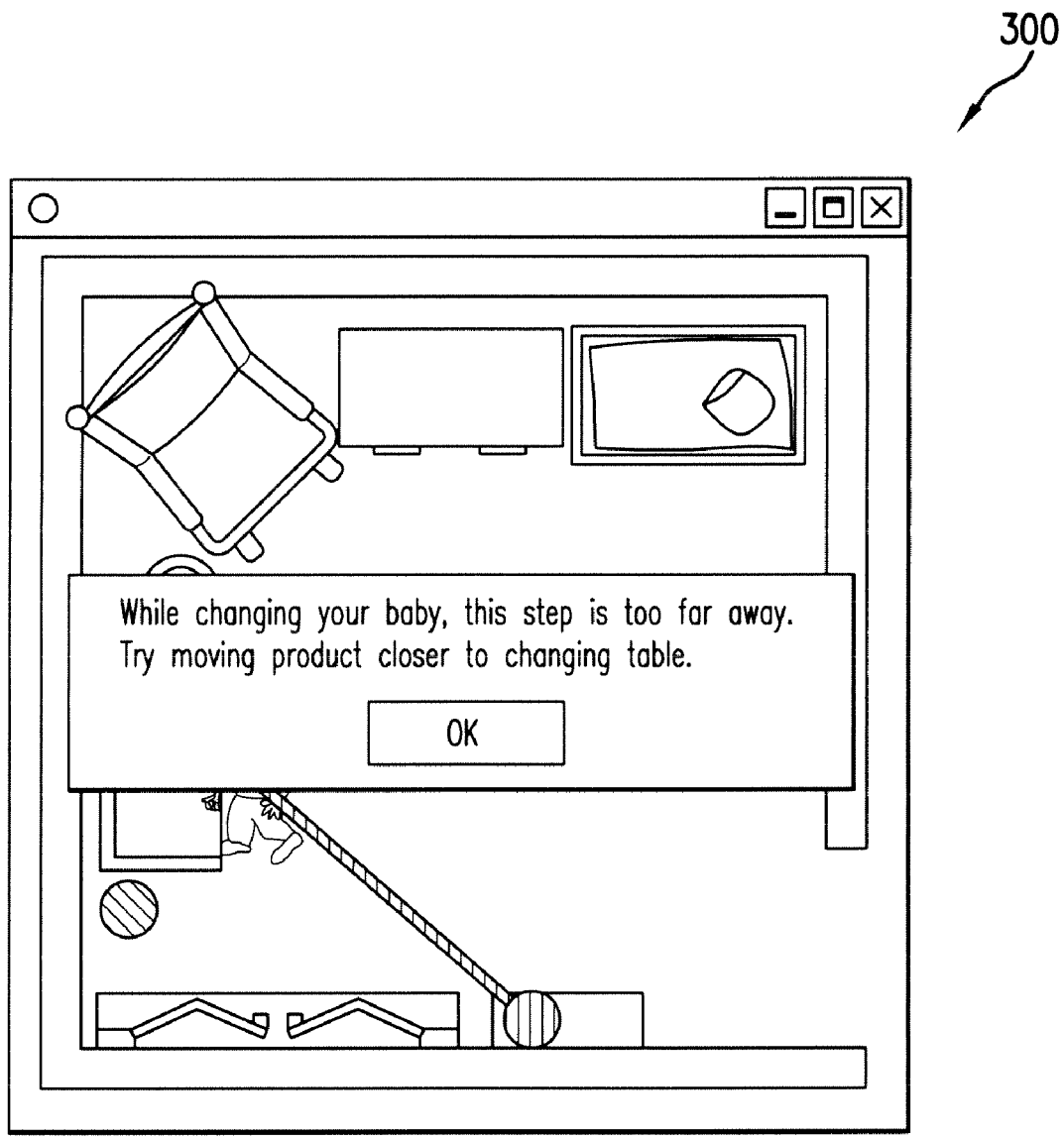

Based on the above simulation and feasibility analysis, the user may virtually rearrange the virtual objects and virtual products in the room and generate a new simulation and feasibility analysis based on the new arrangement of virtual products within the room space. In FIG. 3f, the user has rearranged virtual product 350 by locating it on dresser 310 on the opposite side of the virtual nursery room 300. Virtual product 354 has been relocated from the floor of the virtual nursery room 300 to the changing table 325. As shown in FIG. 3g, the feasibility analysis based on this room configuration indicates virtual product 350 is still located too far from the changing table 325 for the baby changing event to be performed safely and efficiently. The user must therefore again virtually rearrange the virtual products in the nursery room space. The feasibility analysis has provided a suggestion to the user to move the product closer to the changing table 325.

Figure 3H:
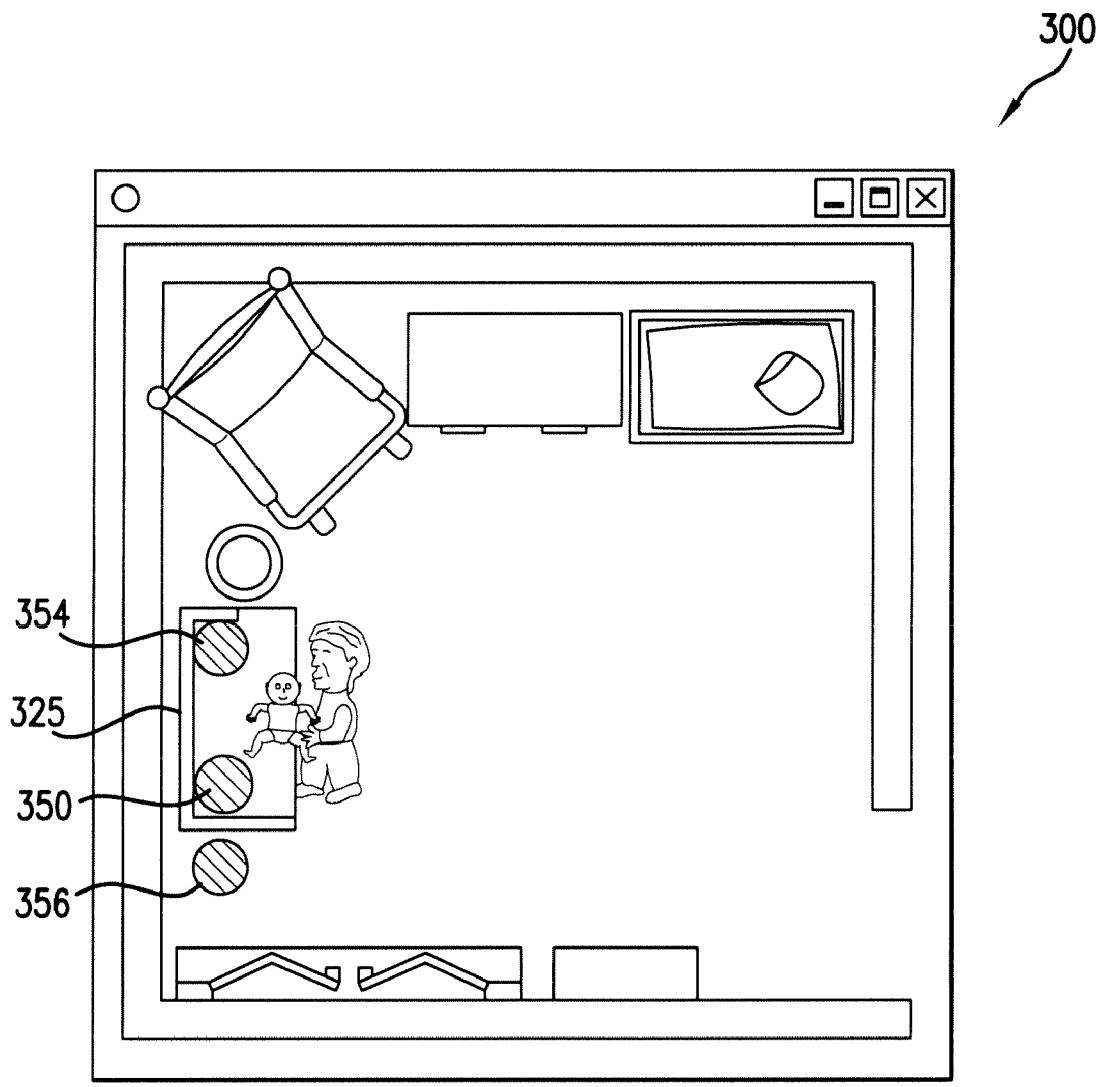
Figure 3I:
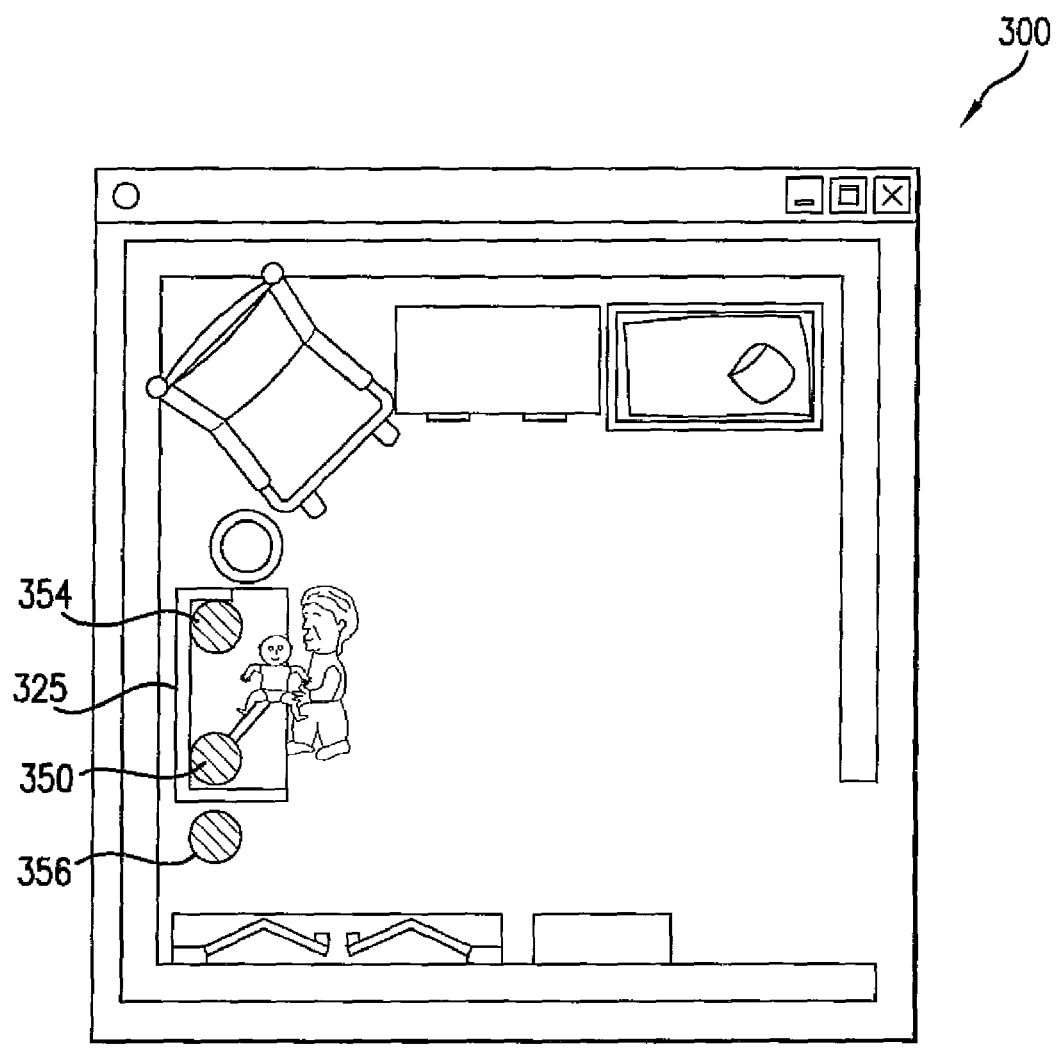

In FIG. 3h, the user has relocated virtual product 350 from dresser 310 to diaper changing table 325. As illustrated in FIG. 3i, the feasibility analysis displays a horizontal line between the location of the virtual product 350 and the location of the simulated baby changing activity to indicate that this particular configuration of virtual product 350 is feasible.

The user has determined a safe and efficient room layout and configuration of virtual products within the room. Thus, the preceding example illustrates how a user can use the room planning system of the present disclosure to determine a safe and efficient room configuration and arrangement of products within the room before actually arranging the room and changing a baby in the room. In this manner, the hassle of having to physically rearrange the nursery room until an efficient layout is achieved can be avoided.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A nursery room planning system, the system comprising:
   a processor; and
   a memory storing instructions for execution by said processor including:
   a virtual nursery room space comprising a virtual representation of an actual nursery room space,
   an environment database comprising a collection of environment data, the environment data comprising attributes of the actual nursery room space, wherein the environment database comprises a collection of virtual objects, the virtual objects comprising virtual representations of furniture, appliances, or fixtures placed in the actual nursery room;
   a product database comprising a collection of virtual disposable products, the virtual disposable products comprising virtual representations of actual disposable products used during a baby changing event;
   a user interface for selecting a virtual disposable product and arranging the virtual disposable product in the virtual nursery room space; and
   a simulation generator for providing a simulation of the baby changing event in the virtual nursery room space, the simulation generator being programmed to provide a feasibility analysis of the baby changing event based at least in part on the arrangement of the virtual disposable product in the virtual room space;
   wherein the feasibility analysis comprises calculating a safety zone surrounding the location adjacent the baby changing event; determining whether the virtual disposable product is located outside the safety zone; and providing a notification that the arrangement of virtual disposable products in the nursery room space is not feasible if the virtual disposable product is located outside the safety zone.

2. The nursery room planning system of claim 1, wherein the feasibility analysis further comprises determining the number of movements an individual will have to make during the baby changing event; comparing the number of movements to a threshold value; and providing a notification that the arrangement of virtual disposable products in the nursery room space is not feasible if the number of movements exceeds the threshold value.

3. The nursery room planning system of claim 1, wherein the feasibility analysis comprises providing a notification of for an alternative arrangement of the virtual disposable product in the nursery room.

4. The nursery room planning system of claim 1, wherein the simulation is interactive.

5. The nursery room planning system of claim 1, wherein the user interface is configured to allow a user to select a virtual object and arrange the virtual object in the virtual nursery room space, the simulation and feasibility analysis being based at least in part on the arrangement of the virtual object in the virtual nursery room space.

6. The nursery room planning system of claim 5, wherein the feasibility analysis comprises suggestions for providing a notification of an alternative arrangement for the virtual object in the virtual nursery room space.

7. The nursery room planning system of claim 1, wherein the environment database or the product database is linked with a retail database.

8. The nursery room planning system of claim 1, wherein the virtual disposable product comprises a virtual representation of a diaper, baby wipe, lotion, baby powder, or clothes.

9. The nursery room planning system of claim 1, wherein the virtual object comprises a virtual representation of a crib, changing table, chair, closet space, dresser, end table, diaper pale or other item of furniture.

10. The nursery room planning system of claim 1, wherein the environment data further comprises user attribute data defining attributes of an anticipated user of the actual nursery room space, the feasibility analysis calculating the safety zone surrounding the location of the baby changing event based at least in part on the user attribute data.

11. The nursery room planning system of claim 1, wherein the simulation generator is configured to provide different feasibility analyses based at least in part on different stages of development for a baby.

12. A method for simulating use of a disposable product during a baby changing event in a nursery room space, the method comprising:
   receiving environment data to include in a virtual room-use simulation, the environment data comprising attributes of a nursery room space;
   receiving disposable product data to include in a virtual room-use simulation, the disposable product data to be used during a baby changing event in the nursery room space;
   generating a virtual nursery room space based on the environment data, the virtual room space comprising a virtual representation of an actual nursery room space;
   generating at least one virtual disposable product based on the disposable product data, the virtual disposable product comprising a virtual representation of an actual disposable product used during the baby changing event;
   receiving a user input directed to the arrangement of the at least one virtual disposable product in the virtual room space;
   generating a simulation of the baby changing event in the virtual nursery room space;
   calculating a safety zone surrounding the location adjacent the baby changing event;
   determining whether the virtual disposable product is located outside the safety zone; and
   providing a notification that the arrangement of virtual disposable products in the nursery room space is not feasible if the virtual disposable product is located outside the safety zone.

13. The method of claim 12, wherein the method comprises:
   determining an alternative arrangement for the at least one virtual disposable product in the nursery room space such that the virtual disposable product falls within the safety zone; and
   providing a notification of the alternative arrangement to a user.

14. The method of claim 12, wherein the method comprises receiving the environment data or the disposable product data from a retail database.

15. The method of claim 12, wherein calculating the safety zone surrounding the location of the baby changing event comprises:
   receiving user attribute data defining attributes of an anticipated user of the actual nursery room space; and
   calculating the safety zone based at least in part on the user attribute data.

16. The method of claim 12, wherein calculating the safety zone surrounding the location of the baby changing event comprises:
   receiving data associated with different stages of development of the baby; and
   calculating the safety zone based at least in part on the data associated with different stages of development of the baby.

17. A method for simulating use of a disposable product during a baby changing event in a nursery room space, the method comprising:
   receiving environment data to include in a virtual room-use, the environment data comprising attributes of a nursery room space;
   receiving disposable product data to include in a virtual room use simulation, the disposable product data to be used during a baby changing event in the room space;
   generating a virtual nursery room space based on the environment data, the virtual room space comprising a virtual representation of an actual nursery room space;
   generating at least one virtual disposable product based on the disposable product data, the virtual disposable product comprising a virtual representation of an actual disposable product used during the baby changing event;
   receiving a user input directed to the arrangement of the at least one virtual disposable product in the virtual room space;
   generating a simulation of the baby changing event in the virtual nursery room space;
   calculating the number of movements an individual will have to make during the baby changing event;
   comparing the number of movements to a threshold value; and
   providing a notification that the arrangement of virtual disposable products in the nursery room space is not feasible if the number of movements exceeds the threshold value.

18. The method of claim 17, wherein the method comprises:
   determining an alternative arrangement for the at least one virtual disposable product in the nursery room space such that the number of movements do not exceed the threshold value; and
   providing a notification of the alternative arrangement to a user.

19. The method of claim 17, wherein the method comprises receiving the environment data or the disposable product data from a retail database.

20. The method of claim 17, wherein calculating the number of movements an individual will have to make during the baby changing event comprises:
   receiving user attribute data defining attributes of an anticipated user of the actual nursery room space; and
   calculating the number of movements based at least in part on the user attribute data.

21. The method of claim 17, wherein calculating the number of movements an individual will have to make during the baby changing event comprises:
   receiving data associated with different stages of development of the baby; and
   calculating the number of movements based at least in part on the data associated with different stages of development of the baby.

* * * * *